United States Patent [19]
Mizuguchi et al.

[11] Patent Number: 5,470,715
[45] Date of Patent: Nov. 28, 1995

[54] COMPOSITION FOR DETERMINATION OF CHLORIDE ION

[75] Inventors: Katsuhiko Mizuguchi; Shin'ichi Teshima; Tsuneo Hanyu, all of Tsuruga, Japan

[73] Assignee: Toyo Boseki Kabushiki Kaisha, Japan

[21] Appl. No.: 176,707

[22] Filed: Jan. 3, 1994

Related U.S. Application Data

[63] Continuation of Ser. No. 733,449, Jul. 22, 1991, abandoned.

[30] Foreign Application Priority Data

| Jul. 23, 1990 | [JP] | Japan | 2-194282 |
| Aug. 10, 1990 | [JP] | Japan | 2-212933 |

[51] Int. Cl.⁶ .................................................. C12Q 1/40
[52] U.S. Cl. ........................... 435/22; 435/7.91; 536/4.1; 536/17.8
[58] Field of Search ............................ 435/22, 18, 7.91; 436/63; 536/4.1, 17.8

[56] References Cited

U.S. PATENT DOCUMENTS

| 4,304,854 | 12/1981 | Nix | 435/14 |
| 4,709,020 | 11/1987 | Rauscher | 536/17.8 |
| 4,963,479 | 10/1990 | Chavez | 435/22 |
| 5,011,923 | 4/1991 | Ono | 536/17.9 |
| 5,068,182 | 11/1991 | Schmidt | 435/22 |

FOREIGN PATENT DOCUMENTS 0275398 7/1988 European Pat. Off. .

OTHER PUBLICATIONS

Ono, T., A New Enzymatic Assay of Chloride In Serum, Clin Chem 34/3 (1988) pp. 552–553.
Yamashita H., Substrate Selective Activation of Histidine Modified Porcine . . . J Biochem 110 (1991) pp. 605–607.

Primary Examiner—Michael G. Wityshyn
Assistant Examiner—Ralph Gitomer
Attorney, Agent, or Firm—Leydig, Voit & Mayer, Ltd.

[57] ABSTRACT

A composition for determination of chloride ion, comprising a maltooligosaccharide derivative possessing modified or non-modified non-reducing terminal and modified reducing terminal, a metal chelating agent, α-amylase and an adjuvant enzyme, provided that the adjuvant enzyme may not be contained when the maltooligosaccharide derivative possesses reducing terminal with a modifying group bound in α-type, which does not require maintenance and control of special instruments and special treatment of waste liquors, affords good analytic efficiency, determination precision and linearity, and is capable of suppressing rise of reagent blank and giving accurate determination values from test samples showing high values.

7 Claims, 4 Drawing Sheets

COMPOSITION FOR DETERMINATION OF CHLORIDE ION

This is a continuation of Ser. No. 07/733,449, filed on Jul. 22, 1991, now abandoned.

BACKGROUND OF THE INVENTION

The present invention relates to compositions for determination of chloride ion. Determination of chloride ion in body fluids provides useful information regarding abnormal transport, absorption and discharge of various electrolytes, and is clinically significant.

Conventionally, determination of chloride ion in body fluids has been generally conducted by a method wherein chloride ion concentration is determined as electric signals, such as the coulometric titration method using a chloride meter and the electrode method using ion-selective electrodes, or colorimetric determination using mercury thiocyanate and iron nitrate. However, special apparatuses are necessary for the former coulometric titration method and the electrode method, which require care for maintenance and control of the instruments, and pose problems such as inferior sample analysis management efficiency. On the other hand, the latter colorimetric determination generates waste liquor containing cyanogen and mercury after the determination, necessitating special treatment therefor. Alternatively, determination of chloride ion by the enzyme method using nonactivated α-amylase and reagents for determination of α-amylase has been adopted recently (Japanese Patent Unexamined Publication No. 126497/1988). In this method, however, a calcium complex is added to a maltooligosaccharide derivative for determination, and poses problems such as prominent rise of reagent blank, poor determination precision, and so on. Also, it has been found that the measurable range is narrower and that dependable measurement values cannot be obtained in the high concentration level which surpasses normal values, posing another problem.

SUMMARY OF THE INVENTION

The present invention resolves the above-mentioned problems conventionally known, and aims at providing a convenient reagent for determination of chloride ion, which does not require maintenance and control of special instruments and special treatment of waste liquors, affords good analytic efficiency, determination precision and linearity, and is capable of suppressing rise of reagent blank and giving accurate determination values from test samples showing high values.

The present inventors conducted intensive studies for the purpose of achieving the objects as described and completed the present invention.

That is, the present invention is a composition for determination of chloride ion, comprising a maltooligosaccharide derivative possessing modified or non-modified non-reducing terminal and modified reducing terminal, a metal chelating agent, α-amylase and an adjuvant enzyme, provided that the adjuvant enzyme may not be contained when the maltooligosaccharide derivative possesses reducing terminal with a modifying group bound in α-type.

DETAILED DESCRIPTION OF THE INVENTION

Figure 1:
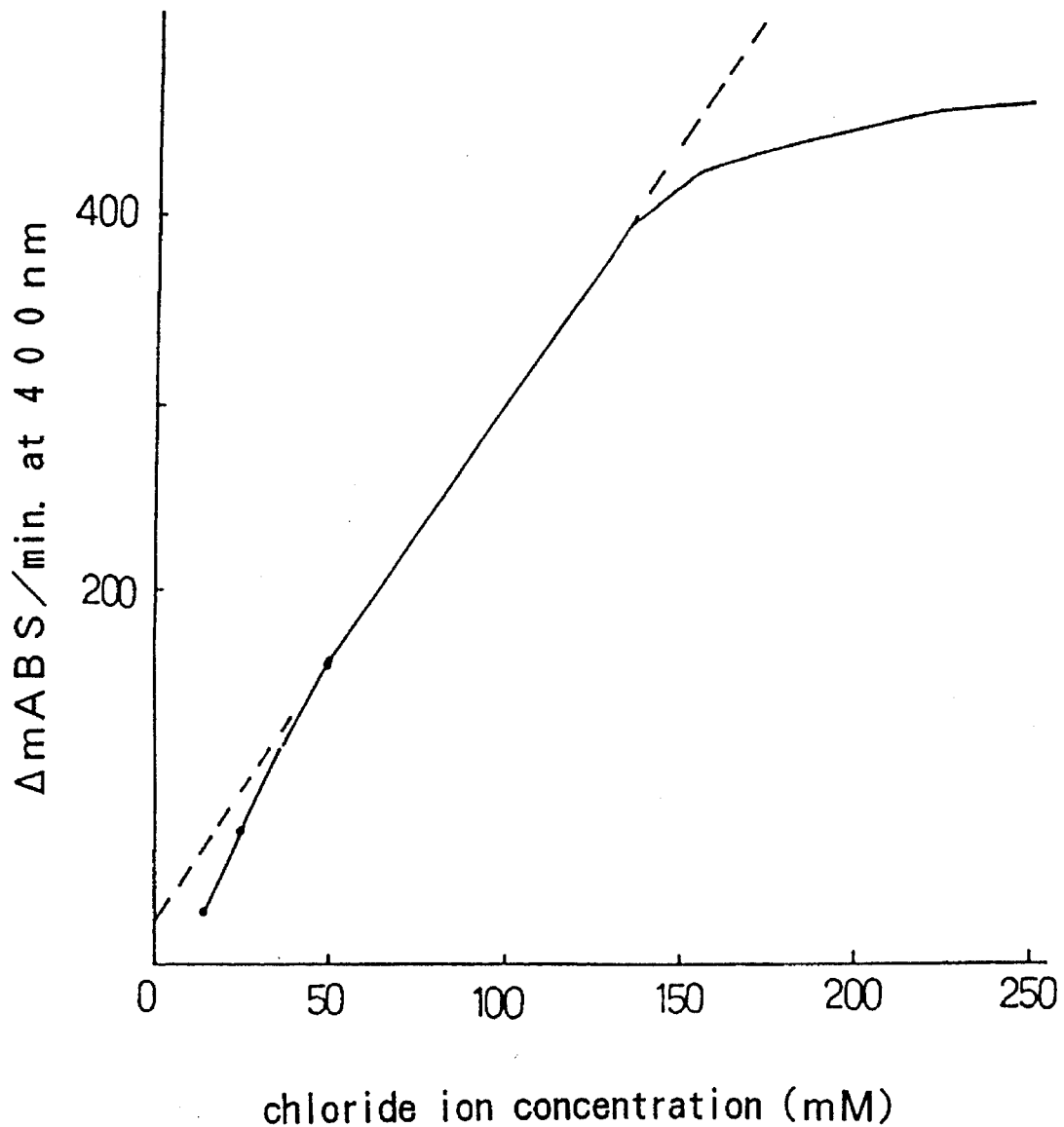
FIG. 1 shows a calibration curve of a KCl solution when 2-chloro- 4-nitrophenyl-β-D-maltopentaoside (GS-β-CNP) is used as a substrate for α-amylase.

The maltooligosaccharide derivative used in the present invention is a maltooligosaccharide derivative of the following formula (I) having modified non-reducing terminal and modified reducing terminal, or a maltooligosaccharide derivative of the following formula (II) having non-modified non-reducing terminal and modified reducing terminal.

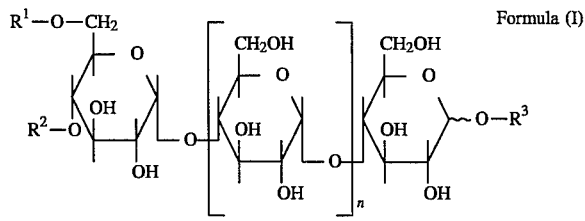

Formula (I)

wherein at least one of $R^1$ and $R^2$ is an alkyl having 1 to 6 carbon atoms, a substituted alkyl, phenyl or substituted phenyl and the other is a hydrogen atom, or $R^1$ and $R^2$ may combinedly form crosslinked methylene (where hydrogen atom of this crosslinked methylene may be substituted by an alkyl having 1 to 6 carbon atoms, a substituted alkyl, phenyl or substituted phenyl), $R^3$ is phenyl or substituted phenyl, and n is an integer of 1 to 8.

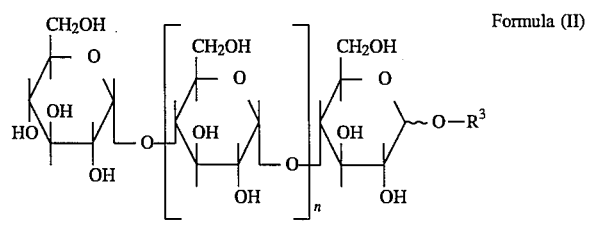

Formula (II)

wherein $R^3$ is phenyl or substituted phenyl and n is an integer of 1 to 8.

As the maltooligosaccharide of the maltooligosaccharide derivative of the invention, there may be mentioned maltotriose, maltotetraose, maltopentaose, maltohexaose, maltoheptaose, maltooctaose, maltononaose and maltodecaose, with preference given to maltotriose, maltotetraose and maltopentaose.

As the modifying group which modifies 4- and/or 6-position hydroxyl(s) of the above-mentioned maltooligosaccharide non-reducing terminal glucose, there may be mentioned an alkyl having 1 to 6 carbon atoms such as methyl, ethyl and propyl; a substituted alkyl such as hydroxymethyl, hydroxyethyl, sulfomethyl, carboxymethyl, sulfoethyl, carboxyethyl, 2-ketopropyl, 2-ketobutyl, 2-ketopentyl, 3-ketopentyl, 4-ketopentyl and benzyl; phenyl; substituted phenyl such as 4-methylphenyl, 4-hydroxyphenyl, 4-carboxyphenyl and 4-sulfophenyl; and crosslinked methylene such as 2-ketopropylidene, 2-ketobutylidene, 3-ketobutylidene, 2-ketopentylidene, 3-ketopentylidene, 4-ketopentylidene, benzylidene, methylidene, ethylidene, isopropylidene, cyclohexylidene, methylsulfinylethylidene, ethylsulfinylethylidene, methanesulfonylethylidene and ethanesulfonylethylidene.

It is particularly desirable that 4- and 6-position hydroxyls of the non-reducing terminal glucose be bound by crosslinked methylene, and further that hydrogen atom of said crosslinked methylene be substituted by an alkyl having a polar group such as carbonyl, sulfinyl and sulfonyl.

As the modifying group which modifies the 1-position hydroxyl of the above-mentioned maltooligosaccharide reducing terminal glucose, there may be mentioned phenyl and substituted phenyl, where the substituted phenyl possesses a substituent such as halogen, nitro and hydroxy. Examples of such substituted phenyl include 4-nitrophenyl, 2-chloro-4-nitrophenyl, 2,6-dichloro-4-nitrophenyl, 2-fluoro-4-nitrophenyl, 2,6-difluoro-4-nitrophenyl, 2-bromo-4-nitrophenyl, 2,6-dibromo- 4-nitrophenyl, 2-nitrophenyl, 2-hydroxy-4-nitrophenyl and 3-hydroxy- 4-nitrophenyl, with preference given to phenyl having nitro and/or halogen atom(s). These groups are bound with the 1-position hydroxyl of the reducing terminal glucose in either $\alpha$-type or $\beta$-type.

In connection with an adjuvant enzyme to be mentioned below, when the adjuvant enzyme is $\beta$-glucosidase alone, it is preferable that a maltooligosaccharide derivative wherein a modifying group is bound in $\beta$-type with the 1-position hydroxyl of the reducing terminal glucose or a mixture of those bound in $\alpha$-type and $\beta$-type be employed. When it has a terminal bound in $\alpha$-type, an adjuvant enzyme is not necessarily required. When an adjuvant enzyme is not contained, the glucose unit number of the maltooligosaccharide derivative is not more than 5, preferably not more than 4.

The maltooligosaccharide derivative of the invention is exemplified by those having reducing terminal with a modifying group bound in either $\alpha$-type or $\beta$-type or a mixture thereof, such as 3-ketobutylidene-2-chloro-4-nitrophenyl-D-maltotrioside, 3-ketobutylidene-2-chloro-4-nitrophenyl-D-maltotetraoside, 3-ketobutylidene- 2-chloro-4-nitrophenyl-D-maltopentaoside, ethylidene-4-nitrophenyl-D-maltotrioside, ethylidene-4-nitrophenyl-D-maltotetraoside, ethylidene-4-nitrophenyl-D-maltopentaoside, benzylidene-4-nitrophenyl-D-maltotrioside, benzylidene-4-nitrophenyl-D-maltotetraoside, benzylidene-4-nitrophenyl-D-maltopentaoside, benzyl-4-nitrophenyl-D-maltotrioside, benzyl-4-nitrophenyl-D-maltotetraoside, benzyl- 4-nitrophenyl-D-maltopentaoside, 2-chloro-4-nitrophenyl-D-maltotrioside, 2-chloro-4-nitrophenyl-D-maltotetraoside, 2-chloro- 4-nitrophenyl-D-maltopentaoside, 4-nitrophenyl-D-maltotrioside, 4-nitrophenyl-D-maltotetraoside and 4-nitrophenyl-D-maltopentaoside.

Examples of the maltooligosaccharide derivative to be used when the composition does not contain an adjuvant enzyme preferably include, for example, 3-ketobutylidene-2-chloro-4-nitrophenyl-$\alpha$-D-maltotrioside, ethylidene-4-nitrophenyl-$\alpha$-D-maltotrioside, benzylidene-4-nitrophenyl-$\alpha$-D-maltotrioside, benzyl-4-nitrophenyl-$\alpha$-D-maltotrioside, 2-chloro-4-nitrophenyl-$\alpha$-D-maltotrioside and 4-nitrophenyl-$\alpha$-D-maltotrioside.

As the metal chelating agent of the invention, there may be mentioned ethylenediaminetetraacetic acid, ethylenediamine-N,N,N',N'-tetraacetic acid, trans-1,2-cyclohexanediamine-N,N,N',N'-tetraacetic acid, dihydroxyethylglycine, diaminopropanoltetraacetlc acid, diethylenetriaminepentaacetic acid, ethylenediaminediacetic acid, ethylenediaminedipropionic acid hydrochloride, hydroxyethylenediaminetriacetic acid, ethylenediaminetetrakis(methylenephosphonic acid), glycol ether diaminetetraacetic acid, hexamethylenediamine-N,N,N',N'-tetraacetic acid, hydroxyethyliminodiacetic acid, iminodiacetic acid, diaminopropanetetraacetic acid, nitrilotriacetic acid, nitrilotripropionic acid, nitrilotris(methylenephosphonic acid), triethylenetetraminehexaacetic acid, 1,2-bis(ortho-aminophenoxy)-ethane-N,N,N',N'-tetraacetic acid, and their univalent metal salts, which can be used alone or in combination.

As the $\alpha$-amylase used in the present invention, there may be mentioned those derived from human pancreas, human saliva, swine, bovine and microorganisms.

Where a maltooligosaccharide derivative having modified non-reducing terminal is used, every $\alpha$-amylase derived from human, other animals: and microorganisms can be employed. Where a maltooligosaccharide derivative having non-modified non-reducing terminal is used, $\alpha$-amylase derived from swine pancreas is preferable.

As the adjuvant enzyme, at least one selected from the group consisting of $\alpha$-glucosidase, $\beta$-glucosidase and glucoamylase is used.

When $\beta$-glucosidase alone is to be used, a maltooligosaccharide derivative wherein a modifying group is bound in $\beta$-type with the 1-position hydroxyl of the reducing terminal glucose or a mixture of those bound in $\alpha$-type and $\beta$-type is employed.

The origin of the $\alpha$-glucosidase used in the present invention is not particularly limited, and those obtained from animals, plants and microorganisms can be used.

The origins of the $\beta$-glucosidase and glucoamylase are not particularly limited, either. For example, $\beta$-glucosidase obtained from almond and glucoamylase obtained from lysopsdelemer can be preferably used.

All kinds of buffers can be used for the composition for determination of chloride ion of the invention, such as phosphate buffer, citrate buffer, borate buffer and Good's buffer. However, those containing chlorides such as hydrochloric acid and sodium chloride are not preferable. pH of the buffer is about 6–8, preferably 7.0.

The composition for determination of chloride ion of the invention contains 0.1–20 mM maltooligosaccharide derivative, 0.01–200 mM chelating agent, 0.05–50 U/ml $\alpha$-amylase, 0–200 U/ml $\alpha$-glucosidase, 0–50 U/ml $\beta$-glucosidase and 0–50 U/ml glucoamylase. When an adjuvant enzyme is to be contained, at least 0.01U/ml thereof is used.

The composition for determination of chloride ion of the invention contains surfactants, antiseptics, stabilizers, etc. as necessary.

In determining chloride ion in a test sample, a reagent comprising the composition of the invention is added to the sample, and resultant phenol or substituted phenol is optically measured. The reagent may be divided into two or more portions and optionally combined. For example, Reagent 1 containing a metal chelating agent, $\alpha$-amylase and an adjuvant enzyme to be contained as necessary and Reagent 2 containing a metal chelating agent and a maltooligosaccharide derivative are prepared, and Reagent 1 is added to the sample, after which Reagent 2 is added for reaction and resultant phenol or substituted phenol is optically measured.

The composition for determination of chloride ion of the invention does not require special treatment of waste liquors, affords good analytic efficiency, determination precision and linearity, and is capable of suppressing rise of reagent blank and permitting accurate and easy determination up to the high concentration level. The reagents of the invention described above can be applied to continuous determination using an automatic analyzer.

The present invention is hereinbelow described by way of examples.

TABLE 1

| | |
|---|---|
| 1 | 3-ketobutylidene-2-chloro-4-nitrophenyl-β-D-maltopenta-oside (3KB-G5-β-CNP) |
| 2 | 4,6-ethylidene-4-nitrophenyl-α-D-maltoheptaoside (E-G7-α-PNP) |
| 3 | 2-chloro-4-nitrophenyl-β-D-maltopentaoside (G5-β-CNP) |
| 4 | 2-chloro-4-nitrophenyl-β-D-maltoheptaoside (G7-β-CNP) |

The results of Example 1 and Comparative Example 1 are shown in Table 2.

TABLE 2

| | | maltooligo-saccharide derivative | increased reagent blank mABS/min. | serum 1 (mM) | serum 2 (mM) | serum 3 (mM) |
|---|---|---|---|---|---|---|
| Example 1 | 1 | 3KB-G5-β-CNP | 3 | 98 | 106 | 116 |
| | 2 | E-G7-α-PNP | 4 | 99 | 108 | 116 |
| | 3 | G5-β-CNP | 12 | 101 | 107 | 115 |
| | 4 | G7-β-CNP | 17 | 100 | 107 | 115 |
| Compara. Ex. 1 (Ca-EDTA added) | 1 | 3KB-GS-β-CNP | 12 | 99 | 107 | 116 |
| | 2 | E-G7-α-PNP | 14 | 98 | 106 | 116 |
| | 3 | G5-β-CNP | 33 | 99 | 108 | 114 |
| | 4 | G7-β-CNP | 45 | 99 | 108 | 115 |

EXAMPLE 1

Using the following reagent and the method, increased reagent blank and chloride ion concentration of 3 kinds of sera were determined.

1. Reagent

| Enzyme reagent solution (referred to as R1) | |
|---|---|
| 0.15M | phosphate buffer (pH 7.0) |
| 38 mM | EDTA |
| 20 U/ml | α-amylase (derived from swine pancreas) |
| 110 U/ml | α-glucosidase |
| 3 U/ml | β-glucosidase |
| Maltooligosaccharide reagent solution (referred to as R2) | |
| 0.15M | phosphate buffer (pH 7.0) |
| 38 mM | EDTA |
| 3.7 mM | maltooligosaccharide derivative (indicated in Table 1) |

In the same manner as above, reagent solutions were prepared by adding 0.75 mM Ca-EDTA to R1 and R2, which were used in Comparative Example 1.

2. Measurement Method

The above-mentioned reagent solution R1 (2 ml) was added to a test sample (25 μl). After keeping the solution at 37° C. for 5 minutes, reagent solution R2 (500 μl) was added thereto, followed by reaction at 37° C. Absorbance was measured at a wavelength of 400 nm, and change in absorbance per one minute was estimated. As for the sera, concentrations were calculated with 70 mM KCl as a standard solution.

As is evident from the results, all of the compositions of the present invention showed less reagent blank increase and good measurement values, in comparison with Comparative Example 1. Particularly, good results were obtained when 3KB-G5-β-CNP and E-G7-α-PNP having modified non-reducing terminal were used.

EXAMPLE 2

Figure 2:
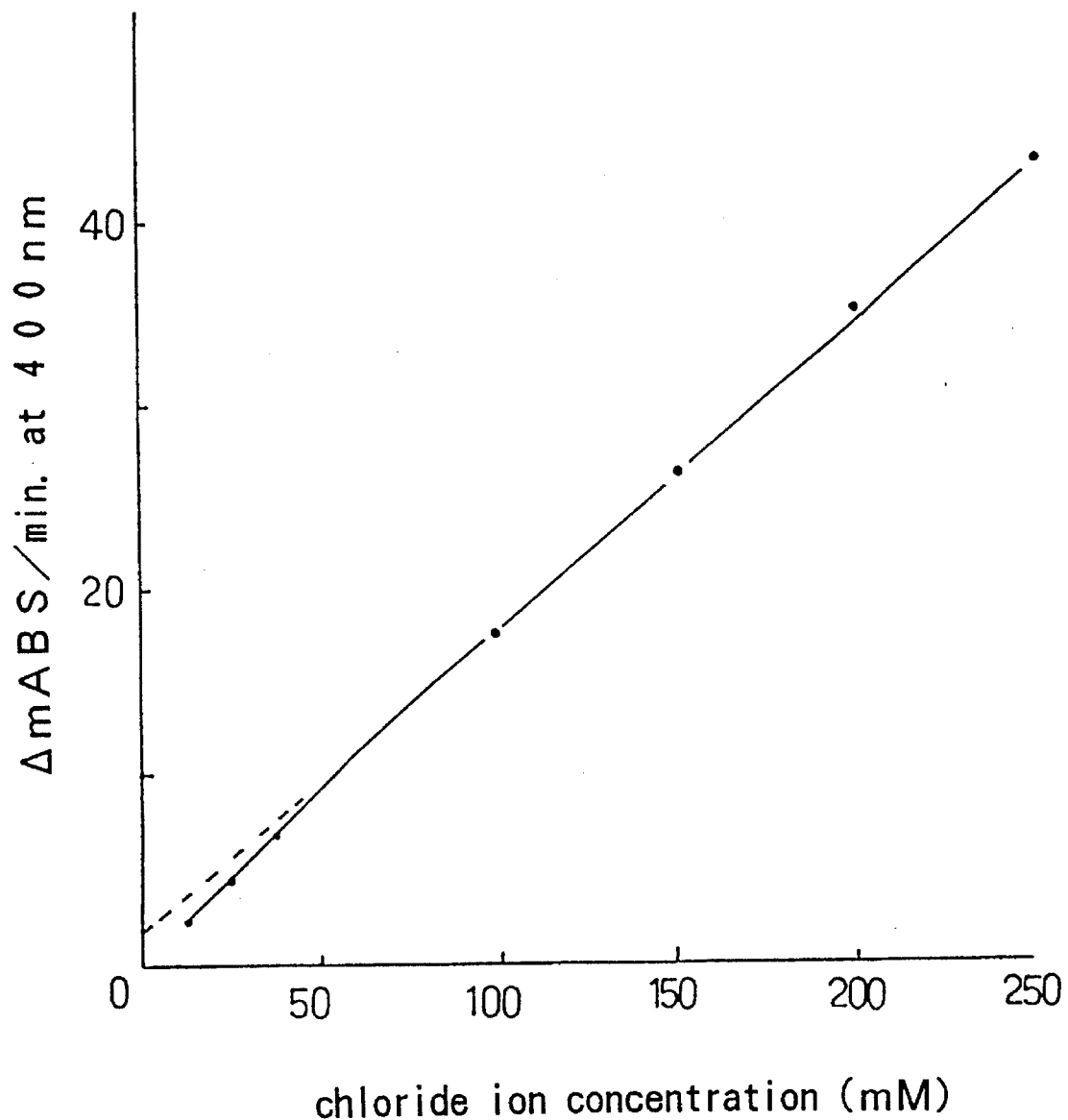
FIG. 2 shows a calibration curve of a KCl solution when 3-ketobutylidene- 2-chloro-4-nitrophenyl-β-D-maltopentaoside (3KB-G5-β-CNP) is used as a substrate for α-amylase.

Using the same reagent and the method as in Example 1 above, and KCl solutions with various concentrations as test samples, linearity and respective measurable range were determined. The results are shown in FIG. 1 and FIG. 2. It is evident from FIG. 2 that use of 3KB-G5-β-CNP having modified non-reducing terminal particularly showed good linearity up to the high concentration level, thereby indicating its potential as a superior composition for chloride ion determination with a wide range of measurability. In addition, FIG. 1 shows that G5-β-CNP having non-modified non-reducing terminal has good linearity in the chloride ion concentration of 50–140 mM.

COMPARATIVE EXAMPLE 2

Figure 3:
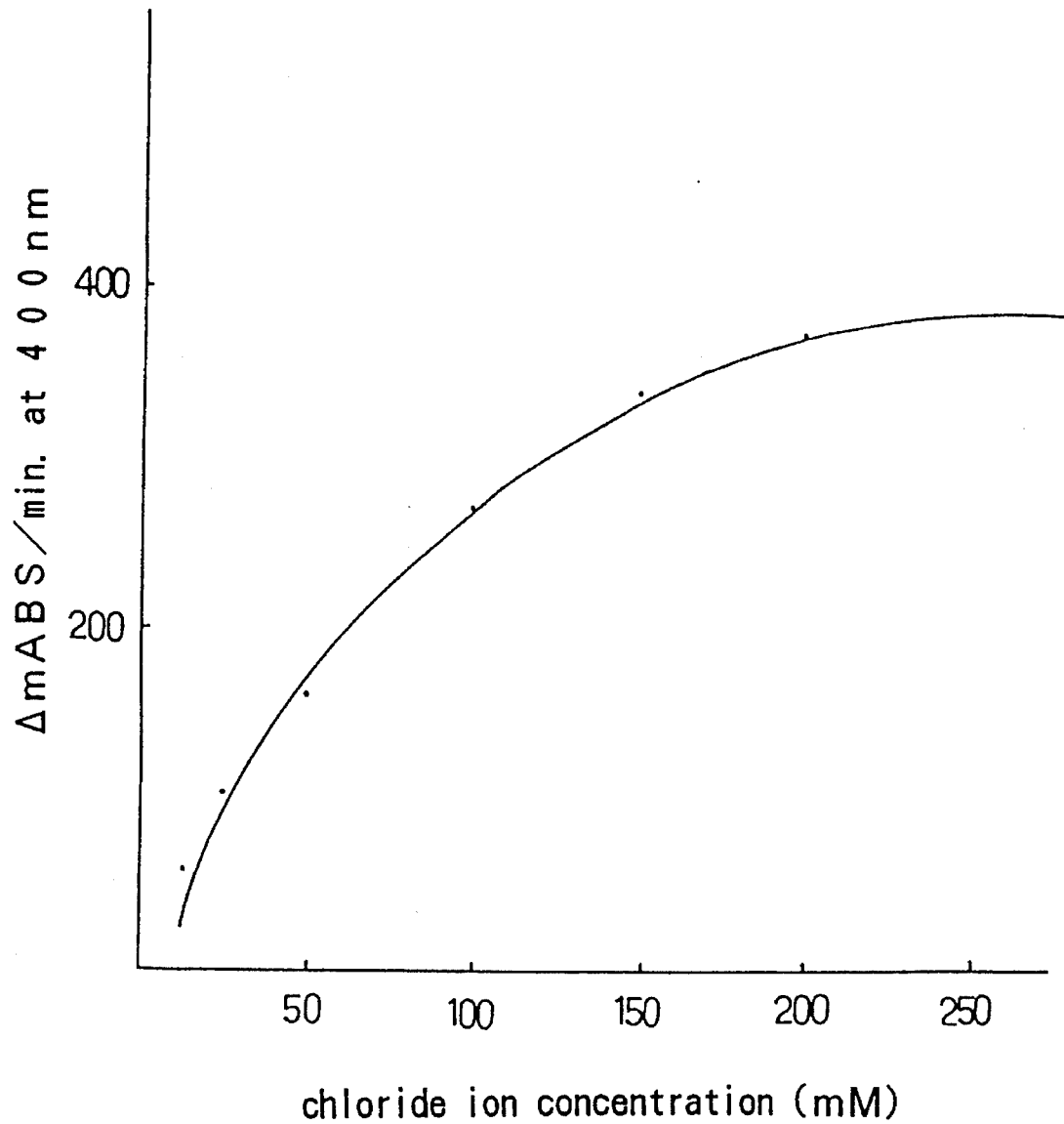
FIG. 3 shows a calibration curve of a KCl solution using KB-G5-β-CNP added with a calcium complex.

Using the same reagent as In Comparative Experiment 1 above and 3KB-G5-β-CNP as a maltooligosaccharide derivative, linearity was examined by the method similar to that of Example 2 above. The results are shown in FIG. 3. The reagent containing a calcium complex showed poor linearity, rendering accurate measurement unattainable.

EXAMPLE 3

Using the following reagent, increased reagent blank and chloride ion concentration of 3 kinds of sera were determined.

1. Reagent

| Enzyme reagent solution (referred to as R1) | |
|---|---|
| 0.15M | phosphate buffer (pH 7.0) |
| 38 mM | EDTA |
| 20 U/ml | α-amylase (derived from swine pancreas) |
| 1 U/ml | glucoamylase |
| 3 U/ml | β-glucosidase |

| Maltooligosaccharide derivative reagent solution (referred to as R2) | |
|---|---|
| 0.15M | phosphate buffer (pH 7.0) |
| 38 mM | EDTA |
| 3.7 mM | maltooligosaccharide derivative (indicated in Table 3) |

In the same manner as above, reagent solutions were prepared by adding 0.75 mM Ca-EDTA to R1 and R2, which were used in Comparative Example 3.

2. Measurement Method

Determination was made in the same manner as in Example 1.

TABLE 3

| 1 | 3KB-G5-β-CNP |
|---|---|
| 2 | G7-β-CNP |
| 3 | 4-nitrophenyl-α-D-maltoheptaoside (G7-α-PNP) |

The results of Example 3 and Comparative Example 3 are shown in Table 4. From the results of Example 3, it is evident that chloride ion can be determined even when glucoamylase is used as an adjuvant enzyme, and that the increased reagent blank became small and good results were obtained particularly when 3KB-G5-β-CNP having modified non-reducing terminal was used. In addition, when G7-β-CNP and G7-β-PNP were used, the increased reagent blank became small and good results were obtained, as compared with Comparative Example 3.

TABLE 4

| | | maltooligo-saccharide derivative | increased reagent blank mABS/min. | serum 1 (mM) | serum 2 (mM) | serum 3 (mM) |
|---|---|---|---|---|---|---|
| Example 3 | 1 | 3KB-G5-β-CNP | 3 | 98 | 108 | 117 |
| | 2 | G7-β-CNP | 76 | 96 | 105 | 117 |
| | 3 | G7-α-PNP | 56 | 96 | 108 | 117 |
| Compara. Ex. 3 | 1 | 3KB-G5-β-CNP | 13 | 98 | 106 | 115 |
| | 2 | G7-β-CNP | 210 | 97 | 104 | 113 |
| | 3 | G7-α-PNP | 198 | 99 | 105 | 110 |

EXAMPLE 4

Using the following reagent and the method, increased reagent blank and chloride ion concentration of 3 kinds of sera were determined.

1. Reagent

| Enzyme reagent solution (referred to as R1) | |
|---|---|
| 0.15M | phosphate buffer (pH 7.0) |
| 38 mM | EDTA |
| 20 U/ml | α-amylase (indicated in Table 5) |
| 110 U/ml | α-glucosidase |
| 3 U/ml | β-glucosidase |

| Maltooligosaccharide reagent solution (referred to as R2) | |
|---|---|
| 0.15M | phosphate buffer (pH 7.0) |
| 38 mM | EDTA |
| 3.7 mM | maltooligosaccharide derivative (indicated in Table 3) |

2. Measurement Method

Determination was made in the same manner as in Example 1.

TABLE 5

| 1 | α-amylase (derived from human saliva) |
|---|---|
| 2 | α-amylase (derived from human pancreas) |
| 3 | α-amylase (derived from swine pancreas) |
| 4 | α-amylase (derived from *Bacittus subtilis*) |

The measurement results are shown in Table 6. Determination of chloride ion was possible even when origin of α-amylase varied. When a maltooligosaccharide having modified non-reducing terminal was used, no difference in reagent blank according to various origins of α-amylase was observed and change in the blank was small.

TABLE 6

| | maltooligo-saccharide derivative | α-amylase | reagent blank change mABS/ min. | serum 1 (mM) | serum 2 (mM) | serum 3 (mM) |
|---|---|---|---|---|---|---|
| 1 | 3KB-β- | 1. human saliva | 3 | 99 | 106 | 115 |

TABLE 6-continued

| | maltooligo-saccharide derivative | α-amylase | reagent blank change mABS/ min. | serum 1 (mM) | serum 2 (mM) | serum 3 (mM) |
|---|---|---|---|---|---|---|
| | G5-CNP | 2. human pancreas | 3 | 99 | 106 | 116 |

TABLE 6-continued

| maltooligo-saccharide derivative | α-amylase | reagent blank change mABS/min. | serum 1 (mM) | serum 2 (mM) | serum 3 (mM) |
|---|---|---|---|---|---|
| | 3. swine pancreas | 3 | 98 | 106 | 115 |
| | 4. B. subtilis | 3 | 97 | 106 | 114 |
| 2 G7-β-CNP | 1. human saliva | 69 | 98 | 107 | 115 |
| | 2. human pancreas | 69 | 96 | 107 | 115 |
| | 3. swine pancreas | 18 | 99 | 109 | 115 |
| | 4. B. subtilis | 76 | 98 | 105 | 118 |
| 3 G7-α-PNP | 1. human saliva | 50 | 98 | 106 | 116 |
| | 2. human pancreas | 53 | 98 | 107 | 115 |
| | 3. swine pancreas | 15 | 96 | 108 | 116 |
| | 4. B. subtilis | 59 | 96 | 107 | 116 |

EXAMPLE 5

Using the following reagent and the method, increased reagent blank and chloride ion concentration of 3 kinds of sera were determined.

1.

① Reagent A

Enzyme reagent solution (referred to as R1)

| | |
|---|---|
| 0.15M | phosphate buffer (pH 7.0) |
| 100 mM | EDTA |
| 21.5 U/ml | α-amylase (derived from swine pancreas) |
| 5 U/ml | β-glucosidase |

Maltooligosaccharide derivative reagent solution (referred to as R2)

| | |
|---|---|
| 0.15M | phosphate buffer (pH 7.0) |
| 100 mM | EDTA |
| 3.5 mM | maltooligosaccharide derivative (indicated in Table 7) |

② Reagent B

Enzyme reagent solution (referred to as R1)

| | |
|---|---|
| 0.15M | phosphate buffer (pH 7.0) |
| 100 mM | EDTA |
| 21.5 U/ml | α-amylase (derived from swine pancreas) |
| 110 U/ml | α-glucosidase |
| 5 U/ml | β-glucosidase |

Enzyme reagent solution (referred to as R2)

| | |
|---|---|
| 0.15M | phosphate buffer (pH 7.0) |
| 100 mM | EDTA |
| 3.5 mM | G5-β-CNP |

2. Measurement Method

The above-mentioned reagent solution R1 (2 ml) was added to a test sample (25 µl). After keeping the solution at 37° C. for 5 minutes, reagent solution R2 (500 µl) was added thereto, followed by reaction at 37° C. Absorbance was measured at a wavelength of 400 nm, and change in absorbance per one minute was estimated. As for the sera, concentrations were calculated with 70 mM KCl as a standard solution. The results are summarized in Table 8.

TABLE 7

2-chloro-4-nitrophenyl-β-D-maltotrioside (G3-β-CNP)
2-chloro-4-nitrophenyl-β-D-maltotetraoside (G4-β-CNP)
2-chloro-4-nitrophenyl-β-D-maltopentaoside (G5-β-CNP)
3-ketobutylidene-2-chloro-4-nitrophenyl-β-D-maltopentaoside (3KB-G5-β-CNP)

TABLE 8

| reagent | maltooligo-saccharide derivative | increased reagent blank mABS/min. | serum 1 (mM) | serum 2 (mM) | serum 3 (mM) |
|---|---|---|---|---|---|
| A | G3-β-CNP | 4 | 96 | 103 | 115 |
| | G4-β-CNP | 6 | 96 | 103 | 118 |
| | G5-β-CNP | 3 | 98 | 103 | 116 |
| | 3KB-G5-β-CNP | 3 | 98 | 104 | 115 |
| B | G5-β-CNP | 15 | 99 | 105 | 115 |

As is evident from the above, good results could be obtained in all cases where β-glucosidase alone was used as an adjuvant enzyme for a maltooligosaccharide having modified reducing terminal bound in β-type. In particular, blank increase was smaller than with α-glucosidase or β-glucosidase as an adjuvant enzyme.

COMPARATIVE EXAMPLE 4

Using the following reagent and the same method as in Example 5, increased reagent blank and chloride ion concentration of 3 kinds of sera were determined.

Enzyme reagent solution (referred to as R1)

| | |
|---|---|
| 0.15M | phosphate buffer (pH 7.0) |
| 100 mM | EDTA |
| 1 mM | Ca-EDTA |
| 21.5 U/ml | α-amylase (derived from swine pancreas) |
| 5 U/ml | β-glucosidase |

Maltooligosaccharide derivative reagent solution (referred to as R2)

| | |
|---|---|
| 0.15M | phosphate buffer (pH 7.0) |
| 100 mM | EDTA |
| 1 mM | Ca-EDTA |
| 3.5 mM | G5-β-CNP |

The results are shown in Table 9.

TABLE 9

| maltooligo-saccharide derivative | increased reagent blank mABS/min. | serum 1 (mM) | serum 2 (mM) | serum 3 (mM) |
|---|---|---|---|---|
| G5-β-CNP | 48 | 97 | 103 | 112 |

It is clear that addition of a calcium complex to a reagent containing β-glucosidase alone as an adjuvant enzyme induces vast increase of reagent blank.

EXAMPLE 6

Figure 4:
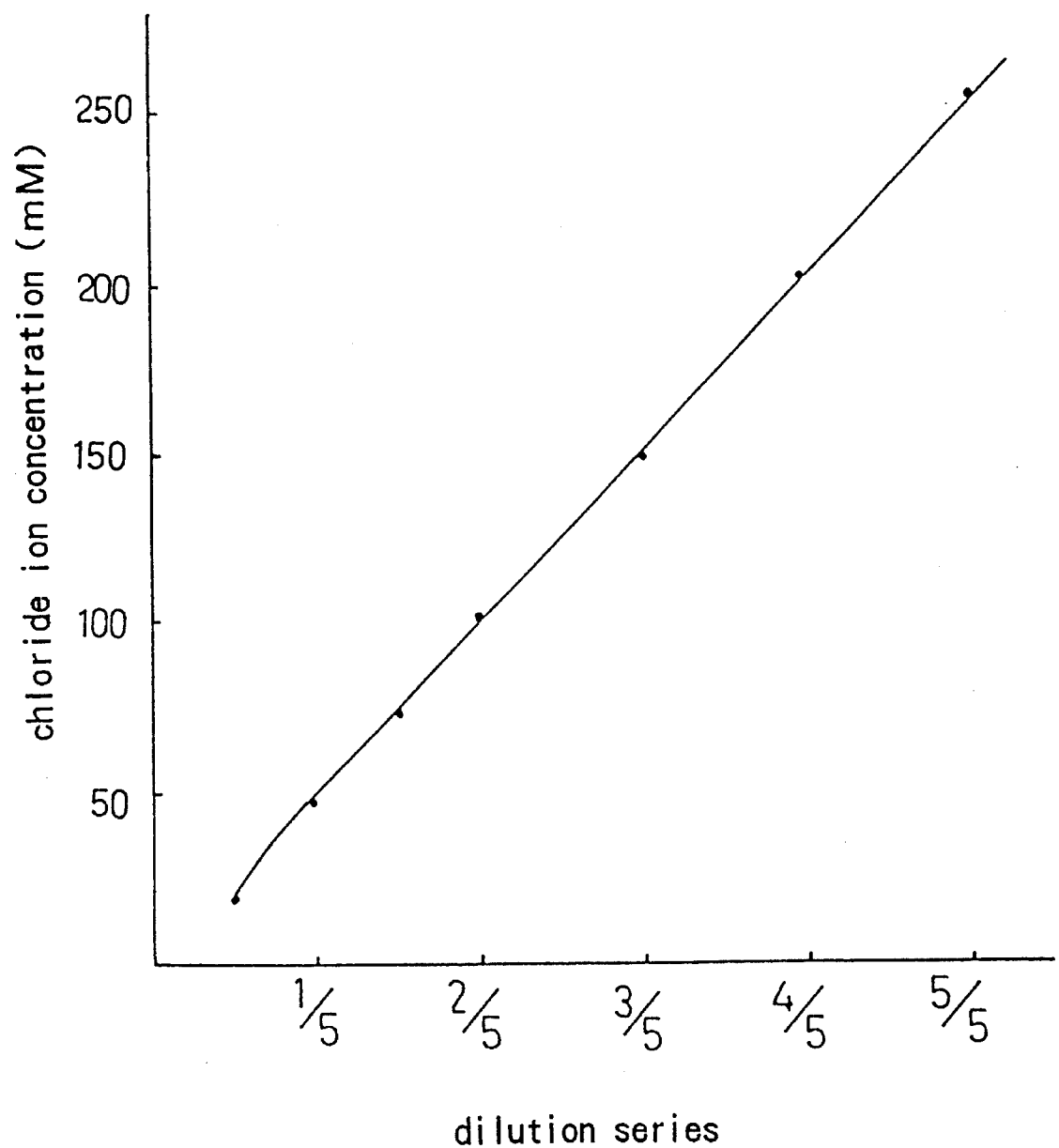
FIG. 4 shows dilution linearity of a KCl solution when β-glucosidase solely is used as an adjuvant enzyme.

Using the same reagent A and the method as in Example 5 mentioned above and G5-β-CNP as a maltooligosaccharide derivative and KCl solutions of various concentrations as a test sample, dilution linearity was determined. The results are shown in FIG. 4.

It is evident that the composition of the invention possesses good linearity and is capable of obtaining accurate determination values from high value samples.

EXAMPLE 7

Using the following reagent and the method, increased reagent blank and chloride ion concentration of 3 kinds of sera were determined.

1. Reagent

| Enzyme reagent solution (referred to as R1) | |
|---|---|
| 0.15M | phosphate buffer (pH 7.0) |
| 100 mM | EDTA |
| 21.5 U/ml | α-amylase (derived from swine pancreas) |
| Maltooligosaccharide derivative reagent solution (referred to as R2) | |
| 0.15M | phosphate buffer (pH 7.0) |
| 100 mM | EDTA |
| 3.5 mM | maltooligosaccharide derivative (indicated in Table 10) |

2. Measurement Method

The same procedure as in Example 1 was followed except that the serum concentration was calculated with 140 mM KCl as a standard solution. The results are summarized in Table 11.

TABLE 10

4-nitrophenyl-α-D-maltotrioside (G3-α-PNP)
4-nitrophenyl-α-D-maltotetraoside (G4-α-PNP)

TABLE 11

| maltooligo-saccharide derivative | increased reagent blank mABS/min. | serum 1 (mM) | serum 2 (mM) | serum 3 (mM) |
|---|---|---|---|---|
| G3-α-PNP | 6 | 95 | 108 | 118 |
| G4-α-PNP | 3 | 93 | 109 | 114 |

As is evident from the above results, increase in reagent blank was small when either G3-α-PNP or G4-α-PNP was used, and good determination results were obtained.

COMPARATIVE EXAMPLE 5

Using the following two kinds of reagents and the method, increased reagent blank and chloride ion concentration of 3 kinds of sera were determined.

1.

| ① Reagent A | |
|---|---|
| Enzyme reagent solution (referred to as R1) | |
| 0.15M | phosphate buffer (pH 7.0) |
| 100 mM | EDTA |
| mM | Ca-EDTA |
| 21.5 U/ml | α-amylase (derived from swine pancreas) |
| Maltooligosaccharide derivative reagent solution (referred to as R2) | |
| 0.15M | phosphate buffer (pH 7.0) |
| 100 mM | EDTA |
| mM | Ca-EDTA |
| 3.5 mM | G3-α-PNP |
| ② Reagent B | |
| Enzyme reagent solution (referred to as R1) | |
| 0.15M | phosphate buffer (pH 7.0) |
| 100 mM | EDTA |
| mM | Ca-EDTA |
| 21.5 U/ml | α-amylase (derived from swine pancreas) |
| 5 U/ml | β-glucosidase |
| 150 U/ml | α-glucosidase |
| Maltooligosaccharide derivative reagent solution (referred to as R2) | |
| 0.15M | phosphate buffer (pH 7.0) |
| 100 mM | EDTA |
| mM | Ca-EDTA |
| 3.5 mM | 4-nitrophenyl-β-D-maltotrioside (G3-β-PNP) |

2. Measurement Method

The reagent solution R1 (2 ml) was added to a test sample (25 μl). After keeping the solution at 37° C. for 5 minutes, reagent solution R2 (500 μl) was added thereto, followed by reaction at 37° C. absorbance was measured at a wavelength of 400 nm, and change in absorbance per one minute was estimated. As for the sera, concentrations were calculated with 140 mM kCl as a standard solution. Measurement was made for the both reagents A and B. The results are summarized in Table 12.

TABLE 12

| | increased reagent blank mABS/min. | serum 1 (mM) | serum 2 (mM) | serum 3 (mM) |
|---|---|---|---|---|
| Reagent A | 29 | 94 | 109 | 110 |
| Reagent B | 74 | 92 | 111 | 114 |

It is evident that addition of calcium in the reagent caused marked increase of blank, and that addition of an adjuvant enzyme further added increase of blank.

According to the present invention, use of a maltooligosaccharide derivative having modified or non-modified non-reducing terminal and modified reducing terminal suppresses increase of reagent blank and permits easy determination of chloride ion up to the high concentration level with good precision.

What is claimed is:

1. A composition for determination of chloride ion, comprising: (1) a maltooligosaccharide derivative possessing a non-reducing terminal and a reducing terminal, the 1-hydroxyl position of the maltooligosaccharide reducing terminal being modified by a phenyl substituted with one or more substituents selected from the group consisting of a hydrogen, halogen, nitro and hydroxy group, and said derivative having the following formula (I):

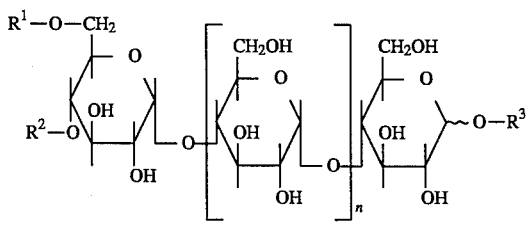

wherein at least one of $R^1$ and $R^2$ is an alkyl having 1 to 6 carbon atoms, a substituted alkyl selected from the group consisting of hydroxymethyl, hydroxyethyl, sulfomethyl, carboxymethyl, sulfoethyl, carboxyethyl, 2-ketopropyl, 2-ketobutyl, 2-ketopentyl, 3-ketopentyl, 4-ketopentyl and benzyl, a phenyl or a substituted phenyl selected from the group consisting of 4-methylphenyl, 4-hydroxyphenyl, 4-carboxyphenyl, and 4-sulfophenyl, and the other is a hydrogen atom, or $R^1$ and $R^2$ may together form crosslinked methylene, $R^3$ is phenyl or substituted phenyl which possesses a substituent selected from the group consisting of halogen, nitro and hydroxy, and n is an integer of 1 to 8, wherein the maltooligosaccharide derivative has a modified non-reducing terminal and a modified reducing terminal; (2) a metal chelating agent; (3) nonactivated α-amylase and (4) an adjuvant enzyme which is an enzyme or combination of enzymes selected from the group consisting of α-glucosidase, β-glucosidase and glucoamylase, provided that the adjuvant enzyme is not present when the maltooligosaccharide derivative possesses a reducing terminal with a modifying group of said 1-hydroxyl position bound in α-orientation and said composition not containing a calcium chelate compound.

2. A composition for determination of chloride ion according to claim 1, containing α-glucosidase and β-glucosidase as the adjuvant enzyme.

3. A composition for determination of chloride ion according to claim 1, containing β-glucosidase alone as the adjuvant enzyme and a maltooligosaccharide derivative having a reducing terminal with a modifying group bound in β-orientation.

4. A composition for determination of chloride ion according to claim 1, wherein the maltooligosaccharide derivative is a maltooligosaccharide derivative having modified non-reducing terminal and modified reducing terminal.

5. A composition for determination of chloride ion according to claim 1, wherein said substituted phenyl of $R^3$ is selected from the group consisting of 4-nitrophenyl, 2-chloro-4-nitrophenyl, 2,6-dichloro-4-nitrophenyl, 2-fluoro-4-nitrophenyl, 2,6-difluoro-4-nitrophenyl, 2-bromo-4-nitrophenyl, 2,6-dibromo-4-nitrophenyl, 2-nitrophenyl, 2-hydroxy-4-nitrophenyl and 3-hydroxy-4-nitrophenyl.

6. A composition for determination of chloride ion, containing a maltooligosaccharide derivative having a modified non-reducing terminal and a reducing terminal, the 1-hydroxyl position of the maltooligosaccharide reducing terminal being modified by a phenyl or substituted phenyl which possesses a substituent selected from the group consisting of halogen, nitro and hydroxy; a metal chelating agent; nonactivated α-amylase; and an adjuvant enzyme which is an enzyme or combination of enzymes selected from the group consisting of α-glucosidase, β-glucosidase and glucoamylase; and said composition not containing a calcium chelate compound.

7. A composition for determination of chloride ion according to claim 1, wherein the adjuvant enzyme is a combination of enzymes selected from the group consisting of α-glucosidase, β-glucosidase and glucoamylase.

\* \* \* \* \*